United States Patent
Boone et al.

(10) Patent No.: US 7,892,762 B2
(45) Date of Patent: *Feb. 22, 2011

(54) METHOD FOR DIAGNOSING IRRITABLE BOWEL SYNDROME AND MONITORING INFLAMMATORY BOWEL DISEASE

(75) Inventors: James Hunter Boone, Christiansburg, VA (US); David Maxwell Lyerly, Blacksburg, VA (US); Tracy Dale Wilkins, Riner, VA (US); Richard Littleton Guerrant, Charlottesville, VA (US)

(73) Assignee: Techlab, Inc., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/486,727

(22) Filed: Jun. 17, 2009

(65) Prior Publication Data

US 2009/0253155 A1 Oct. 8, 2009

Related U.S. Application Data

(60) Continuation of application No. 10/629,975, filed on Jul. 30, 2003, now Pat. No. 7,560,240, which is a division of application No. 10/002,842, filed on Nov. 14, 2001, now Pat. No. 7,192,724.

(60) Provisional application No. 60/248,288, filed on Nov. 14, 2000.

(51) Int. Cl.
*G01N 33/00* (2006.01)

(52) U.S. Cl. .......... 435/7.1; 435/7.21; 435/7.92; 435/7.94; 436/514; 436/533; 436/534

(58) Field of Classification Search .............. None
See application file for complete search history.

(56) References Cited

U.S. PATENT DOCUMENTS 5,124,252 A * 6/1992 Guerrant et al. .......... 435/7.24

OTHER PUBLICATIONS

Pool et al. (Gut, 1993, 34, 46-50).*
Sugi et al. (The American Journal of Gastroenterology, vol. 91, No. 5, 927-934, 1996).*
Kruzel et al. (Advances in Experimental Medicine and Biology, 1998, 443, pp. 167-173-Abstract Only).*
Peen et al. (Gut, 1993, 34, 56-62).*

* cited by examiner

*Primary Examiner*—Lisa V Cook
(74) *Attorney, Agent, or Firm*—Shook, Hardy & Bacon L.L.P.

(57) ABSTRACT

A method for aiding in differentiating irritable bowel syndrome from inflammatory bowel disease by determining the level of total endogenous human lactoferrin in clinical specimens, such as feces, mucus and bile, wherein an elevated level of lactoferrin substantially precludes diagnoses of IBS and other noninflammatory etiologies, and a kit usable in such method are provided. Further provided is a method for quantitating the level of total endogenous human lactoferrin in clinical specimens, such as feces, mucus and bile, to monitor gastrointestinal inflammation in persons having inflammatory bowel disease.

14 Claims, No Drawings

METHOD FOR DIAGNOSING IRRITABLE BOWEL SYNDROME AND MONITORING INFLAMMATORY BOWEL DISEASE

CROSS-REFERENCE TO RELATED APPLICATIONS

This application is a continuation application of U.S. patent application Ser. No. 10/629,975, which is a divisional of U.S. application Ser. No. 10/002,842 filed on Nov. 14, 2001, which claims the benefit of priority to U.S. Provisional Application Ser. No. 60/248,288, filed on Nov. 14, 2000, each of which is hereby incorporated by reference.

BACKGROUND

The present invention relates to the clinical differentiation and monitoring of gastrointestinal illnesses. More particularly, the present invention relates to a method for aiding in differentiating irritable bowel syndrome from inflammatory bowel disease by determining the level of total endogenous human lactoferrin in clinical specimens, such as feces, mucus and bile, wherein an elevated level of lactoferrin substantially precludes diagnoses of IBS and other noninflammatory etiologies, and a kit usable in such method. The present invention further relates to a method for quantitating the level of total endogenous human lactoferrin in clinical specimens, such as feces, mucus and bile, to monitor gastrointestinal inflammation in persons having inflammatory bowel disease.

Gastrointestinal illnesses are responsible for an extensive loss of life worldwide. For instance, diarrhea is a major cause of morbidity and mortality in developing countries with an estimated one billion cases of diarrheal diseases and five million deaths in children per year. In the United States, eight to twelve million people are treated each year for infectious diarrhea making up 2.5% of total hospitalizations and resulting in 10,000 deaths. Other gastrointestinal illnesses include inflammatory bowel disease (IBD) and irritable bowel syndrome (IBS). Annual evaluation for these disorders in the United States results in 1 and 3.5 physician visits, respectively. Symptoms of active IBS and those of active IBD are similar and, accordingly, the two diseases often present nearly identically. However, IBD can be a severe, life-threatening condition and thus quick, accurate differential diagnosis is extremely important.

IBD, comprised of both Crohn's Disease (CD) and ulcerative colitis (UC), is characterized by a chronic immune-mediated inflammatory response that results in histologic damage to the intestinal lining. Both CD and UC exhibit large numbers of leukocytes that migrate to the mucosa and into the intestinal lumen. Both diseases oscillate between active (i.e., presence of intestinal inflammation) and inactive (i.e., minimal to no intestinal inflammation) stages of disease activity. Active IBD can include symptoms such as bloody diarrhea, abdominal pain, and fever. The inactive stage has minimal to no intestinal inflammation and lacks severe gastrointestinal illness.

Patients who have active IBD but who exhibit mild signs and symptoms may be difficult to distinguish from patients with active IBS, an intestinal disorder of motility and the intestinal nervous system. Unlike IBD, IBS does not involve intestinal inflammation. In persons with IBS, the intestine appears normal upon endoscopic examination and leukocytes are not present in the mucosa or in fecal specimens. Symptoms can mimic those of IBD and include bloating, diarrhea, constipation, and severe and often debilitating abdominal pain. It is estimated that at least 35 million Americans suffer from IBS.

The similarity in symptoms between IBS and IBD renders rapid diagnosis rather difficult. However, given the potential severity of untreated IBD, differential diagnosis is crucial. The diagnosis of gastrointestinal illnesses, in general, is aided by diagnostic tests such as enzyme-linked immunosorbant assays (ELISAs), latex agglutination and lateral flow immunoassay. These tests are rapid and inexpensive methods for detecting markers in feces for enteric pathogens and inflammation. One marker of particular interest that has been found to be most specific for leukocytes in fecal specimens is lactoferrin. Human lactoferrin is an 80 kilodalton glycoprotein. This iron-binding protein is secreted by most mucosal membranes. It is a major component of the secondary granules found in polymorphonuclear neutrophils (PMNs), a primary component of the acute inflammatory response. Other hematopoietic cells such as monocytes and lymphocytes, do not contain lactoferrin, whereas various bodily secretions contain levels in the mg/mL range. During the process of inflammation, PMNs infiltrate the mucosa lining of the small and large intestine. This increase in the number of activated tissue leukocytes and exudation of plasma from ulcerated mucosa results in an increase in the level of lactoferrin found in feces. The protein is resistant to proteolysis and, as such, it provides a useful non-invasive fecal marker of intestinal inflammation.

Human lactoferrin has been used as a marker for fecal leukocytes in a number of applications. For instance, fecal lactoferrin has been used as a marker for leukocytes to distinguish noninflammatory diarrhea from inflammatory diarrhea, as disclosed in U.S. Pat. No. 5,124,252 (the "252 patent"). Noninflammatory diarrhea caused by agents such as rotavirus, Norwalk-like agents and cholera, typically causes minimal to no intestinal damage and patients respond readily to oral rehydration. Inflammatory diarrheas include those caused by enteric pathogens such as *Clostridium difficile, Shigella* species, *Salmonella* species, *Campylobacter jejuni* and *Entamoeba histolytica* and those that have no clearly defined infectious agent such as CD and UC. U.S. Pat. No. 5,124,252 discloses an in vitro test for fecal leukocytes which aids in distinguishing inflammatory from noninflammatory diarrhea. The >252 patent discloses testing fecal samples suspected of containing leukocytes with an assay that utilizes an antibody for lactoferrin to determine the presence of leukocytes in the fecal sample.

Human lactoferrin also has been used as a marker for diagnosis of inflammatory gastrointestinal disorders, colon polyp and colorectal cancer as disclosed in U.S. Pat. No. 5,552,292 (the "292 patent"). However, neither the method of the '252 patent nor that of the '292 patent disclose utility in distinguishing IBS and IBD. The samples tested by the assay of the '252 patent are samples suspected of containing leukocytes. This suspicion is owed to the patient presenting with diarrhea. However, 25-50% of persons having IBD do not present with diarrhea and, thus, the '252 patent does not relate to diagnosing etiology in such patients. As for the '292 patent, the disclosed method utilizes a 1:100 sample dilution which does not allow for accurate quantitation of lactoferrin levels. Further, the '292 patent discloses using partial forms of molecules for testing and not total endogenous lactoferrin, again affecting the accuracy of the quantitation. The method of the '292 patent also does not relate to utilizing lactoferrin levels to distinguish between IBD and IBS. The population tested in the '292 patent, while including persons with UC and CD, did not include persons having IBS. Therefore, there remains a need in the diagnostic industry for a noninvasive method for differentially diagnosing IBD and IBS which utilizes human lactoferrin as a marker.

Given that lactoferrin has been shown to be a good marker for fecal leukocytes, tests have been developed to aid physicians in determining the presence of fecal lactoferrin. One such test is the LEUKO-TEST®, manufactured by TechLab, Inc. of Blacksburg, Va. The LEUKO-TEST® is a latex agglutination test for detecting fecal lactoferrin. It is noninvasive and demonstrates active intestinal inflammation thus providing physicians evaluating patients with diarrhea with important information concerning the severity of any underlying bacterial infection.

Even though the LEUKO-TEST® is useful for evaluating gastrointestinal illnesses, the latex agglutination format provides some limitations. In large hospitals with a high volume of specimens, batching is preferred. A format such as ELISA is more useful for batching than latex agglutination and has the option of automation. It also may indicate severity of the disease and the effectiveness of medical treatments, by measuring the levels of fecal lactoferrin. In the case of IBD, a rise in fecal lactoferrin may provide an early indicator for active disease and the effects of medical treatments.

Currently, there are no known in vitro diagnostic aids to assist treating physicians, or other clinical personnel, in distinguishing between IBD and IBS. Accordingly, there remains a need for an in vitro diagnostic aid to assist treating physicians and other clinical personnel in distinguishing between these two commonly presenting diseases.

SUMMARY

Accordingly, the present invention provides a non-invasive method for differentiating irritable bowel syndrome (IBS) from inflammatory bowel disease (IBD) wherein the presence of fecal lactoferrin is used as a detection marker for fecal leukocytes, elevated levels of which substantially preclude diagnoses of IBS and other noninflammatory etiologies, and a kit therefor. This rapid diagnosis then may be utilized by healthcare professionals to prescribe proper treatment. The present invention further provides immunoassays, e.g., enzyme-linked immunoassays (ELISAs), that utilize antibodies specific to human lactoferrin for the measurement of total endogenous lactoferrin in clinical specimens, such as human feces, mucus and bile, and a kit usable in such immunoassays. Still further, the present invention provides to a method for quantitating the levels of lactoferrin from endogenous sources, particularly, infiltrating leukocytes, to monitor gastrointestinal inflammation in persons having IBD.

It has been shown that fecal lactoferrin has utility as a marker for distinguishing patients with IBD from those with less severe IBS. To aid physicians and other clinical personnel in utilizing this discovery, immunoassays are provided herein for detecting elevated levels of fecal lactoferrin and for quantitating fecal lactoferrin levels. Specifically, a qualitative enzyme-linked immunosorbent assay (ELISA) is provided wherein polyclonal antibodies against total endogenous human lactoferrin are utilized to detect elevated levels of fecal lactoferrin. The qualitative assay of the present invention permits the screening of patients presenting with symptoms common between IBS and IBD. If elevated levels of fecal lactoferrin are detected, a diagnosis of IBS is substantially precluded. It will be understood and appreciated by those of skill in the art that a qualitative immunoassay such as a lateral flow dipstick that utilizes both monoclonal and polyclonal antibodies to total endogenous lactoferrin also may be used to indicate the absence or presence of gastrointestinal inflammation. Such is contemplated to be within the scope hereof.

The qualitative assay of the present invention provides a test that is easy to use, simple to read, and accurate for distinguishing active IBD from active IBS. To substantiate equivalence of the ELISA to predicate devices, test results have been compared to microscopy results and to results from the latex agglutination test manufactured by TechLab, Inc. of Blacksburg, Va. under the brand name LEUKO-TEST®. To this end, two studies were conducted involving a total of 166 fecal specimens. When compared with microscopy, the assay of the present invention presented a sensitivity of 80.0% in the first study and 94.1% in the second study. The assay further presented a specificity of 90.0% in the first study and 51.7% in the second study. In the same studies, when compared with the LEUKO-TEST®, sensitivity results were 90.5% in the first study and 89.6% in the second study. Specificity results were 86.4% in the first study and 57.5% in the second study.

For the evaluation of the qualitative assay of the present invention as a diagnostic aid for IBD and IBS patients, fecal samples from subjects having IBD were collected and the assay results were compared with those from healthy control subjects and subjects having clinically defined cases of IBS. The IBD group included subjects having both ulcerative colitis (UC) and Crohn's disease (CD). The fecal lactoferrin levels determined in these subjects were used to establish the preferred predictive optical density for the assay of 0.200 $OD_{450}$. Results indicated that the assay was positive (i.e., an $OD_{450}$ greater than or equal to 0.200) for 86.0% of fecal specimens from subjects with active IBD and was consistently negative (i.e., an $OD_{450}$ less than 0.200) for specimens from subjects with active IBS and from healthy control subjects. ("$OD_{450}$" as used herein indicates an optical density measured at 450 nm on a single wavelength spectrophotometer.)

In an additional clinical evaluation the qualitative assay of the present invention was compared to clinical assessments of IBD and active IBS subjects. In the IBD group, there were ninety-two subjects with active disease (fifty-one with active CD and forty-one with active UC) and fifty-seven with inactive disease. In the active group, a total of eighty subjects, or 87.0%, tested positive with the assay of the present invention. In the inactive group, thirty-two, or 56.1%, tested positive. Of the fifty-one IBD subjects with active CD, forty-four, or 86.3%, tested positive. Of the forty-one IBD subjects with active UC, thirty-six, or 87.8%, tested positive with the assay. All thirty-one subjects, or 100%, with active IBS, and all fifty-six healthy control subjects, or 100%, tested negative with the assay of the present invention.

Research findings thus support the use of the qualitative assay of the present invention as an in vitro diagnostic aid for detecting elevated levels of lactoferrin as a detection marker for fecal leukocytes and an indicator of inflammation. Other intestinal ailments, including many gastrointestinal infections and colorectal cancer, often result in elevated levels of lactoferrin in fecal specimens and these specimens likely will test positive with the assay of the present invention. Therefore, a diagnosis of active IBD cannot be established solely on the basis of a positive result with the assay of the present invention. However, a positive result with the assay of the present invention will permit the substantial preclusion of a diagnosis of IBS or other noninflammatory etiologies.

Also provided is a quantitative ELISA wherein polyclonal antibodies against total endogenous human lactoferrin are utilized to quantitate levels of gastrointestinal inflammation through comparison to a standard curve generated using purified human lactoferrin. These levels then may be utilized to monitor the effects of medical treatments in patients having IBD.

In the quantitative assay of the present invention, the level of total endogenous human lactoferrin in clinical specimens is determined through comparison to a standard curve generated using purified human lactoferrin and analyzed by linear regression. Research findings show that the level of fecal lactoferrin in persons having IBS was lower than the mean fecal lactoferrin level determined in healthy persons indicating the absence of gastrointestinal inflammation. However, the levels of fecal lactoferrin in IBD patients determined using the quantitative assay of the present invention were significantly higher than the mean fecal lactoferrin level of healthy persons. Thus, the quantitative assay of the present invention will permit the monitoring of patients having IBD as the levels of fecal lactoferrin may be determined over the course of medical treatments to determine whether or not the treatment is effective in decreasing or eliminating gastrointestinal inflammation.

Additional aspects of the invention, together with the advantages and novel features appurtenant thereto, will be set forth in part in the description which follows, and in part will become apparent to those skilled in the art upon examination of the following, or may be learned from the practice of the invention. The aspects and advantages of the invention may be realized and attained by means, instrumentalities and combinations particularly pointed out in the appended claims.

DETAILED DESCRIPTION

The present invention is directed to diagnostic test methods for aiding in differentiating irritable bowel syndrome (IBS) from inflammatory bowel disease (IBD) and for monitoring persons having IBD, and a kit usable in such methods. The particular embodiments described herein are intended in all respects to be illustrative rather than restrictive. Alternative embodiments will become apparent to those skilled in the art to which the invention pertains without departing from its scope.

The qualitative diagnostic test method of the present invention is an immunoassay for the detection of elevated levels of lactoferrin, a detection marker for fecal leukocytes, and an indicator of intestinal inflammation. The method can be used as an in vitro diagnostic aid to help identify patients with active IBD and rule out those with active IBS, which is non-inflammatory. The lactoferrin specific immunoassays can be used to differentiate IBS from IBD by measuring the level of total endogenous lactoferrin. "Total endogenous lactoferrin," as that term is used herein, comprises lactoferrin derived from endogenous sources, particularly infiltrating leukocytes (i.e., leukocytes, plasma, bile and mucosal secretions).

In the preferred embodiment, the qualitative immunoassay of the present invention is an enzyme-linked immunoassay (ELISA). The ELISA format provides the clinical laboratory with a simple-to-use test that is familiar to medical and clinical laboratory personnel. The test will aid a treating physician and other clinical personnel in distinguishing active IBD, which can become life-threatening and requires special treatment, from IBS, which is not life-threatening and which utilizes lifestyle modifications as therapy. The test is easy to perform, utilizing a one component substrate system and a total incubation time of seventy-five minutes. The qualitative assay of the present invention preferably utilizes a specimen dilution of 1:400 and optical densities of 0.200 $OD_{450}$ and 0.160 at $OD_{450/620}$. It will be understood and appreciated by those of skill in the art that a qualitative immunoassay such as a lateral flow dipstick that utilizes both monoclonal and polyclonal antibodies to total endogenous lactoferrin also may be used to indicate the absence or presence of gastrointestinal inflammation. Such is contemplated to be within the scope hereof.

The following are examples of procedures which have been utilized to establish the preferred qualitative and quantitative assays according to the present invention. The following examples are merely exemplary and not presented by way of limitation.

1. Qualitative Assay a. Establishment of Optimal Sample Dilution Factor and Optical Density The assay of the present invention was designed and developed to detect levels of fecal lactoferrin at a lower level detectable by predicate devices, specifically the LEUKO-TEST®. The lower limit of detection of the LEUKO-TEST® is 256 ng/mL with purified human lactoferrin. In the LEUKO-TEST®, a specimen dilution of 1:50 and a minimum limit of detection of 256 ng/mL provides a lower limit of detection in fecal specimens of approximately 12 μg/mL. A specimen dilution of 1:400 and a minimum detection limit for the assay of the present invention of 32 ng/mL also provides a lower limit of detection in fecal specimens of approximately 12 μg/mL. Accordingly, a 1:400 specimen dilution was chosen for the assay of the present invention. Similarly, an optical density of 0.200 $OD_{450}$ for the assay was chosen. (As used herein, $OD_{450}$ indicates an optical density obtained spectrophotometrically at 450 nm on a single wavelength spectrophotometer.)

It will be understood and appreciated by those of skill in the art that the preferred dilution factor and optical densities have been determined based upon reagents currently available and deemed to be optimal. However, reagents other than those now desired may become improved and desirable over time. Variations in reagents may produce preferable/optimal dilution factors and/or optical densities other than those determined herein. Such variations are contemplated to be within the scope of the present invention. The key to determining optimal values is based upon sensitivity as more fully described below.

To verify that the 1:400 specimen dilution provides the most desirable sensitivity with the current reagents, 121 fecal specimens were analyzed comparing a 1:400 dilution to a 1:800 dilution. (Sensitivity is calculated herein by dividing the number of samples taken from subjects with IBD which produce a positive result in the assay by the number of samples taken from subjects with IBD.) Test results additionally were evaluated comparing $OD_{450}$ values of 0.200 to $OD_{450}$ values of 0.300. Results were compared with microscopy for fecal leukocytes and with the LEUKO-TEST®. The results are summarized in Tables I-VIII below.

TABLE I

Comparison of the ELISA with microscopy for fecal leukocytes using a 1:400 dilution and an OD450 of 0.200

| ELISA vs. microscopy (N = 121) | Microscopy positive | Microscopy negative |
|---|---|---|
| ELISA positive | 32 | 42 |
| ELISA negative | 2 | 45 |

Relative Sensitivity 94.0%
Relative Specificity 52.0%
Correlation 64.0%

TABLE II

Comparison of the ELISA with microscopy for fecal leukocytes using a 1:400 dilution and an OD450 of 0.300

| ELISA vs. microscopy (N = 121) | Microscopy positive | Microscopy negative |
|---|---|---|
| ELISA positive | 31 | 31 |
| ELISA negative | 3 | 56 |

Relative Sensitivity 91.0%
Relative Specificity 64.0%
Correlation 72.0%

TABLE III

Comparison of the ELISA with microscopy for fecal leukocytes using a 1:800 dilution and an OD450 of 0.200

| ELISA vs. microscopy (N = 121) | Microscopy positive | Microscopy negative |
|---|---|---|
| ELISA positive | 30 | 31 |
| ELISA negative | 4 | 56 |

Relative Sensitivity 88.0%
Relative Specificity 64.0%
Correlation 77.0%

TABLE IV

Comparison of the ELISA with microscopy for fecal leukocytes using a 1:800 dilution and an OD450 of 0.300

| ELISA vs. microscopy (N = 121) | Microscopy positive | Microscopy negative |
|---|---|---|
| ELISA positive | 26 | 24 |
| ELISA negative | 8 | 63 |

Relative Sensitivity 77.0%
Relative Specificity 72.0%
Correlation 74.0%

TABLE V

Comparison of the ELISA with the LEUKO-TEST ® using a 1:400 dilution and an OD450 of 0.200

| ELISA vs. LEUKO-TEST ® (N = 121) | LEUKO-TEST ® positive | LEUKO-TEST ® negative |
|---|---|---|
| ELISA positive | 43 | 31 |
| ELISA negative | 5 | 42 |

Relative Sensitivity 89.6%
Relative Specificity 57.5%
Correlation 70.2%

TABLE VI

Comparison of the ELISA with the LEUKO-TEST ® using a 1:400 dilution and an OD450 of 0.300

| ELISA vs. LEUKO-TEST ® (N = 121) | LEUKO-TEST ® positive | LEUKO-TEST ® negative |
|---|---|---|
| ELISA positive | 41 | 21 |
| ELISA negative | 7 | 52 |

Relative Sensitivity 85.0%
Relative Specificity 71.2%
Correlation 77.0%

TABLE VII

Comparison of the ELISA with the LEUKO-TEST ® using a 1:800 dilution and an OD450 of 0.200

| ELISA vs. LEUKO-TEST ® (N = 121) | LEUKO-TEST ® positive | LEUKO-TEST ® negative |
|---|---|---|
| ELISA positive | 39 | 22 |
| ELISA negative | 9 | 51 |

Relative Sensitivity 81.3%
Relative Specificity 69.9%
Correlation 74.4%

TABLE VIII

Comparison of the ELISA with the LEUKO-TEST ® using a 1:800 dilution and an OD450 of 0.300

| ELISA vs. LEUKO-TEST ® (N = 121) | LEUKO-TEST ® positive | LEUKO-TEST ® negative |
|---|---|---|
| ELISA positive | 34 | 16 |
| ELISA negative | 14 | 57 |

Relative Sensitivity 70.8%
Relative Specificity 78.1%
Correlation 75.2%

In summary, a fecal specimen dilution of 1:400 and an assay $OD_{450}$ of 0.200 showed the highest level of sensitivity with the current reagents. Accordingly, these conditions were determined to be optimal for the assay of the present invention. Normal fecal specimens contain low levels of lactoferrin and the 1:400 dilutions have been determined to be optimal in detecting an increase in lactoferrin over background levels. The use of dilutions lower than 1:400 may result in positive test results due to the presence of normal lactoferrin levels.

b. Collection of Specimens and Preparation of Dilutions

Standard collection and handling procedures typically used for fecal specimens for culture may be used in collecting samples for the assay of the present invention. In the preferred embodiment, fecal specimens are to be tested within twenty-four hours of collection. However, if the assay is not to be performed within forty-eight hours of collection, it is preferred that the specimens be stored at −20° C. or lower. Additionally, it is preferred that collected specimens be transported and diluted in the Diluent as soon as possible after collection and, once diluted, that the specimens be stored at between about 2° C. and about 8° C. It is preferred that the specimens be mixed (i.e., using a vortex mixer) thoroughly prior to performing the assay of the present invention. This includes complete mixing of the specimen prior to transfer to the Diluent, as more fully described below, as well as complete mixing of the diluted specimen prior to performing the assay.

The following method was used to prepare a diluted specimen from a liquid fecal specimen. Two plastic tubes were set up for each specimen to be tested. For each specimen, 950 μL of 1× Diluent (prepared as more fully described below) subsequently was added to each of the two tubes. Using a transfer pipette, one drop (i.e., approximately 50 μL) of liquid fecal specimen was added to one of the tubes and thoroughly mixed using a vortex mixer. Subsequently, one drop of the diluted specimen was transferred into the second tube containing 950 μL of 1× Diluent (prepared as more fully described below).

The result was a 1:400 dilution of the specimen in the second tube. Thus, only the second tube was used for the remainder of the test procedure.

The following method was used to prepare a diluted specimen from a formed or solid fecal specimen. Two plastic tubes were set up for each specimen to be tested. For each specimen, 1.9 mL of 1× Diluent (prepared as more fully described below) was added to only one of the two tubes. Subsequently, 0.10 g of fecal specimen were added to this tube (1:10) and thoroughly mixed using a vortex mixer. Next, 950 μL of the 1× Diluent (prepared as more fully described below) was added to the second tube and one drop (i.e., approximately 50 μL) of the previously diluted specimen is transferred into the second tube. The result was a 1:400 dilution of the specimen in the second tube. Thus, only the second tube was used for the remainder of the test procedure.

The specimen in the second tube prepared according to either of the above procedures was mixed in a vortex mixer for approximately ten seconds and subsequently stored at between about 2° C. and about 8° C. until the remainder of the test procedure was performed. Prior to transferring the diluted specimen into a microtiter well according to the test procedure, as more fully described below, the specimen was thoroughly mixed in the vortex mixer once again. This procedure sought to ensure thorough mixing of the specimen.

c. Necessary Test Reagents and Preparation Thereof

A number of reagents were necessary to carry out the preferred embodiment of the qualitative assay of the present invention. These reagents included 10× Diluent, 1× Diluent, Conjugate, Substrate, Positive Control, Wash Buffer Solution and Stop Solution. The 10× Diluent was a 10× concentrate of buffered protein solution containing 0.2% thimerosal as a preservative. The Diluent was supplied as a 10× concentrate. Therefore, to prepare the 1× Diluent necessary for the assay of the present invention, a total volume of 400 mL was diluted by adding 40 mL of the 10× concentrate to 360 mL of deionized water. Any unused 1× Diluent was stored at between about 2° C. and about 8° C.

The Conjugate used with the assay of the present invention preferably comprises rabbit polyclonal antibody specific for human lactoferrin conjugated to horseradish peroxidase and in a buffered protein solution containing 0.02% thimerosal as a preservative. The Substrate used with the assay of the present invention preferably comprises a solution containing tetra-methyl-benzidine substrate and peroxidase. The Positive Control used with the assay of the present invention preferably comprises human lactoferrin in a buffered protein solution containing 0.02% thimerosal as a preservative. The Stop Solution used with the assay of the present invention preferably comprises 0.6 N sulfuric acid.

The Wash Buffer Solution used with the assay of the present invention was supplied as a 20× concentrate containing phosphate buffered saline, detergent and 0.2% thimerosal as a preservative. To prepare the 1× Wash Solution necessary for the assay of the present invention, a total volume of one liter of concentrate was diluted by adding 50 mL of the concentrate to 950 mL of deionized water. Any unused 1× Wash Solution was stored at between about 2° C. and about 8° C.

Microassay plates containing twelve strips and eight wells per strip are preferred for the assay of the present invention. Each specimen and each control requires a single coated well. To prepare the plates, each strip was coated with purified polyclonal antibody specific for lactoferrin. Microassay plates were stored with desiccant.

All reagents were stored at room temperature prior to use in the assay of the present invention.

The present invention includes a kit designed and prepared for carrying out the quantitative assay. In the preferred embodiment, the kit contains 40 mL 10× Diluent, 7 mL Conjugate, 14 mL Substrate, 3.5 mL Positive Control, 50 mL Wash Buffer Solution, 7 mL Stop Solution and one microassay plate stored with desiccant. The assay of the present invention utilizes antibodies to human lactoferrin. The microassay plate supplied with the kit contains immobilized polyclonal antibody against lactoferrin. The detecting antibody consists of polyclonal antibody conjugated to horseradish peroxidase.

d. Test Procedure

To perform the qualitative assay of the present invention, initially the number of wells needed was determined. Each specimen or control required one well and, therefore, the number of wells was determined accordingly. Next, one drop (i.e., about 50 μL) of Positive Control was added to a single well designated the Positive Control Well and one drop (i.e., about 50 μL) of 1× Diluent was added to a single well designated the Negative Control Well. Subsequently, two drops (i.e., about 100 μL) of 1:400 diluted specimen (prepared according to the above procedure) was added to a third well and all wells were incubated at about 37EC ("2° C.) for approximately thirty minutes. After incubation, the contents of the assay wells was discarded into a discard pan.

Next, each well was washed using 1× Wash Solution (prepared as described above) and placed in a squirt bottle with a fine-tipped nozzle. In this manner, the 1× Wash Solution was directed into the bottom of each of the wells with some force. Each well was filled with the 1× Wash Solution and the contents thereof subsequently discarded into a discard pan. The microassay plate was then inverted and slapped on a dry paper towel. This wash procedure was performed a minimum of four times using a dry paper towel each time. If any particulate matter was observed in the wells, the washing procedure was continued until all the matter was removed.

Subsequently, one drop (i.e., about 50 μL) of Conjugate was added to each well and the wells were incubated at about 37° C. (±2° C.) for approximately thirty minutes. After incubation, the contents of the assay wells were discarded into a discard pan and the washing procedure was repeated. Next, two drops (i.e., about 100 μL) of Substrate were added to each well and the wells were gently tapped to mix the contents. The wells were then incubated at room temperature for approximately fifteen minutes. The wells were gently tapped a couple of times during the incubation period.

Next, one drop (i.e., 50 μL) of Stop Solution was added to each well and the wells were gently tapped. The wells were allowed to sit at room temperature for about two minutes before reading. The addition of Stop Solution converted the blue color to a yellow color which could then be quantified by measuring the optical density at 450 nm on a microplate ELISA reader. The instrument was blanked against the negative control and the underside of each well was wiped before measuring the optical density. Optical densities ($OD_{450}$ and $OD_{450/620}$) were recorded for the Positive Control Well, the Negative Control Well and each specimen tested. ("$OD_{450/620}$" as used herein indicates an optical density obtained spectrophotometrically at 450/620 nm on a dual wavelength spectrophotometer.) Readings of duplicate wells were averaged before the results were interpreted.

The specified test procedure represents the preferred embodiment as optimal results are obtained by following the procedure specified because the reagents, concentrations, incubation conditions, and processing specifications have been optimized for sensitivity and specificity. Accordingly, alterations of the specified procedure and/or of the indicated test conditions may affect the sensitivity and specificity of the test.

e. Quality Control

The positive and negative control must meet certain criteria for the test to be valid. First of all, the Positive Control Well must be a visible yellow color and, when read on a spectrophotometer, it must have an $OD_{450}$ and $OD_{450/620}$>0.500. The Negative Control Well must have an $OD_{450}$<0.200 or an $OD_{450/620}$<0.160. To ensure that carryover has not occurred, testing should be repeated if a sample gives a weak positive result (i.e, <0.400) and is adjacent to a strong positive well.

f. Interpretation of Results

Optical densities were measured at 450 nm on a single wavelength spectrophotometer and at 450/620 nm on a dual wavelength spectrophotometer. On a single wavelength spectrophotometer, an $OD_{450}$ of less than 0.200 indicated a negative result and an $OD_{450}$ of greater than or equal to 0.200 indicated a positive result. On a dual wavelength spectrophotometer, an $OD_{450/620}$ of less than 0.160 indicated a negative result and an $OD_{450/620}$ of greater than or equal to 0.160 indicated a positive result.

A positive test result indicated the specimen contained elevated levels of lactoferrin when compared with a reference value established for healthy control subjects. A negative test result indicated the specimen did not contain elevated levels of lactoferrin relative to samples from healthy control subjects.

g. Results

One hundred forty-nine subjects having IBD were tested according to the above procedure. Seventy-seven of the subjects, or 51.7%, were male and seventy-two of them, or 48.3%, were female. The tested male to female ratio closely approximates the 1:1 ratio observed in the general IBD patient population. Ages of the subjects ranged from 3 years to 78 years and thirty-two subjects, or 22%, were 16 years of age or younger. Seventy-seven subjects, or 51.7%, had CD and seventy-two of them, or 48.3% had UC.

Thirty-one subjects having IBS were tested. Six of the subjects, or 19.3%, were male and twenty-five of them, or 80.7%, were female. The tested male to female ratio closely approximates the 1:3 ratio observed in the general IBS population. Ages of the subjects ranged from 19 years to 78 years.

Fifty-six healthy subjects also were tested as controls. Twenty-eight of the subjects, or 50%, were male and twenty-eight of them, or 50%, were female. Ages of the subjects ranged from infants to 79 years. A summary of the tested subject population is illustrated in Table IX.

TABLE IX

| Summary of Subject Population | |
|---|---|
| Summary of Clinical Histories (N = 180) | Total Subjects |
| Total number of IBD patients | 149 |
| No. Males | 77 |
| No. Females | 72 |

TABLE IX-continued

| Summary of Subject Population | |
|---|---|
| Summary of Clinical Histories (N = 180) | Total Subjects |
| Total number of patients with CD | 77 |
| No. Males | 43 |
| No. Females | 34 |
| Total number of patients with UC | 72 |
| No. Males | 34 |
| No. Females | 38 |
| Total number of patients with irritable bowel syndrome | 31 |
| No. Males | 6 |
| No. Females | 25 |
| Total number of healthy persons | 56 |
| No. Males | 28 |
| No. Females | 28 |

Fecal specimens were collected from each enrolled subject and stored at −70° C. until tested. Sample consistencies ranged from liquid to solid, numbers for which are illustrated in Table X for each subject group. As can be seen, forty-five of the IBD specimens were liquid specimens, sixty-two were semi-solid specimens, and forty-two were solid specimens. One of the IBS specimens was a liquid specimen, thirteen were semi-solid specimens, and seventeen were solid specimens. All of the specimens from healthy control subjects were solid.

TABLE X

| Summary of Specimen Consistencies for Each Subject Group | |
|---|---|
| Summary of Stool Specimens (N = 236) | Total Specimens |
| Total number of IBD patients (CD and UC) | 149 |
| Total number of liquid specimens | 45 |
| Total number of semi-solid specimens | 62 |
| Total number of solid specimens | 42 |
| Total number of patients with IBS | 31 |
| Total number of liquid specimens | 1 |
| Total number of semi-solid specimens | 13 |
| Total number of solid specimens | 17 |
| Total number of healthy persons | 56 |
| Total number of liquid specimens | 0 |
| Total number of semi-solid specimens | 0 |
| Total number of solid specimens | 56 |

The level of fecal lactoferrin in each specimen was determined using the qualitative lactoferrin ELISA as previously described. A specimen dilution of 1:400 was used. Results were reported as positive if an optical density of greater than or equal to 0.200 was observed. Conversely, results were reported as negative if an optical density of less than 0.200 was observed.

Of the IBD subject group, ninety-two subjects had active disease and fifty-seven had inactive disease. Of the active group, a total of eighty subjects, or 87.0%, tested positive in the assay. Of the inactive group, a total of thirty-two subjects, or 56.1%, tested positive. Of the forty-one subjects having active UC, a total of thirty-six subjects, or 87.8% tested positive in the assay. Of the fifty-one subjects having active CD, forty-four, or 86.3%, tested positive. All thirty-one patients having active IBS and all fifty-six healthy control subjects tested negative in the assay. A summary of assay test results is illustrated in Table XI and various individual comparisons are illustrated in Tables XII, XIII and XIV, as more fully described below.

TABLE XI

Summary of ELISA test Results for CD, UC, Active IBS, and Healthy Control Subjects

| Clinical Assessments N = 236 | Total | ELISA Positive | ELISA Negative |
|---|---|---|---|
| Total IBD | 149 | 75.2% (112) | 24.8% (37) |
| Active | 92 | 87.0% (80) | 13.0% (12) |
| Inactive | 57 | 56.1% (32) | 43.0% (25) |
| Total CD | 77 | 77.9% (60) | 22.1% (17) |
| Active | 56 | 86.3% (44) | 13.7% (7) |
| Inactive | 26 | 61.5% (16) | 38.5% (10) |
| Total UC | 72 | 72.2% (52) | 27.7% (20) |
| Active | 41 | 87.8% (36) | 12.2% (5) |
| Inactive | 31 | 51.6% (16) | 48.4% (15) |
| Total Active IBS | 31 | 0 | 100.0% (31) |
| Total Healthy Persons | 56 | 0 | 100.0% (56) |

When distinguishing samples from active IBD subjects from subject samples having IBS or from healthy control samples, the ELISA exhibited a sensitivity of 87% and specificity of 100%. Sensitivity was calculated by dividing the number of persons having IBD and testing positive in the ELISA by the number of subjects having IBD. Specificity was calculated by dividing the number of subjects having IBD and testing positive in the ELISA by the number of subjects testing positive in the ELISA. The predictive positive and negative values were 100% and 87.9%, respectively, and the correlation was 93.3%. These results are summarized in Table XII.

TABLE XII

Statistical Evaluation using the ELISA to Distinguish Active IBD from IBS/Healthy Control Subjects

| N = 179 | Active IBD | IBS/Healthy Controls |
|---|---|---|
| ELISA positive | 80 | 0 |
| ELISA negative | 12 | 87 |

Sensitivity 87.0%
Specificity 100%
Predictive Positive Value 100%
Predictive Negative Value 87.9%
Correlation 93.3%

When distinguishing samples from active UC subjects from subject samples having IBS or from healthy control subjects, the ELISA exhibited a sensitivity of 87.8% and a specificity of 100%. The predictive positive and negative values were 100% and 94.6%, respectively, and the correlation was 96.1%. These results are summarized in Table XIII.

TABLE XIII

Statistical Evaluation using the ELISA to Distinguish Active UC from IBS/Healthy Control Subjects

| N = 128 | Active UC | IBS/Healthy Controls |
|---|---|---|
| ELISA positive | 36 | 0 |
| ELISA negative | 5 | 87 |

Sensitivity 87.8%
Specificity 100%
Predictive Positive Value 100%
Predictive Negative Value 94.6%
Correlation 96.1%

When distinguishing subject samples having active CD from subject samples having IBS or from healthy control samples, the ELISA exhibited a sensitivity of 86.3% and a specificity of 100%. The predictive positive and negative values were 100% and 92.6%, respectively, and the correlation was 94.9%. These results are summarized in Table XIV.

TABLE XIV

Statistical Evaluation using the ELISA to Distinguish Active CD from IBS/Healthy Control Subjects

| N = 138 | Active UC | IBS/Healthy Controls |
|---|---|---|
| ELISA positive | 44 | 0 |
| ELISA negative | 7 | 87 |

Sensitivity 86.3%
Specificity 100%
Predictive Positive Value 100%
Predictive Negative Value 92.6%
Correlation 94.9% h. Reproducibility and Precision

The inter-assay variation was determined by analyzing eight lactoferrin-negative and eight lactoferrin-positive fecal specimens over a three day period. The average % Coefficient of Variation (CV) was 23.5% for the positive specimens and 7.4% for the negative specimens. The intra-assay variation was determined by analyzing twelve fecal specimens using six replicates in one lot of kits. The intra-assay analysis ranged in % CV from 2.7 to 24.0 with an average of 8.7%.

2. Quantitative Assay

In the quantitative assay of the present invention, fecal specimens preferably are serially diluted ten-fold and added to microtiter wells containing immobilized polyclonal antibodies against human lactoferrin. If endogenous lactoferrin is present, it will bind to the antibodies during an incubation at approximately 37° C. Following the incubation, conjugate comprised of polyclonal antibodies coupled to horseradish peroxidase enzyme is added and allowed to bind to captured lactoferrin. Unbound conjugate is then washed from the well and a component substrate (e.g., tetra-methyl-benzidene and hydrogen peroxide) is added for color development. Following the substrate incubation, 0.6N sulfuric acid is added to quench the reaction and the absorbance or optical density (OD) is obtained spectrophotometrically at 450 nm on a single wavelength device. Fecal lactoferrin concentrations are determined by comparison to a standard curve generated using purified human lactoferrin.

a. Preparation of Standard Curve

A 1 mg/mL stock solution of purified human lactoferrin, manufactured by Sigma Immunochemicals of St. Louis, Mo., was prepared using 10 mg of lactoferrin dissolved in 10 mL of sterile phosphate buffered saline (PBS) at a pH of 7.4. Serial two-fold dilutions of lactoferrin were made using the range of approximately 6 to 100 ng/mL in Diluent. For the analysis, 0.1 mL of each standard was assayed in duplicate. Optical densities ($OD_{450}$) were determined and plotted versus lactoferrin concentration to generate standard curves. The linear portion of the curve was determined by linear regression analysis using the Log-Log method (Microsoft EXCEL, Microsoft R Office). The lowest dilution of specimen that gave an $OD_{450}$ within the linear portion of the curve was used to determine the lactoferrin concentration. The final concentration was obtained by multiplying the concentration by the dilution factor.

b. Quantitative Test Procedure

In order to assess the ability of the quantitative ELISA to measure the level of fecal lactoferrin, two fecal specimens collected six weeks apart from six female and five male adults were diluted and then spiked with lactoferrin to a concentration of 25 ng/mL. The "Estimated Lactoferrin" that was determined represents the level of lactoferrin determined from a standard curve generated with the quantitative ELISA. The % Variation represents the difference between the "Actual" amount used to spike the sample and the "Estimated" amount. Under these conditions, the variations ranged from 1.0% to 85.8% for females and 8.8% to 47.0% for males. Results showed a higher percent variation in female adults as compared to male adults. The stool samples that showed a higher variation had higher levels of lactoferrin prior to spiking. The results are illustrated in Tables XV and XVI below.

TABLE XV

Stool samples of female adult subjects spiked to a final concentration of 25 ng/mL

| Patient ID # | Actual Lactoferrin (ng/ML) | Estimated Lactoferrin (ng/mL) | Variation (%) |
|---|---|---|---|
| 1 | 25 | 15.4 | 38.4 |
| 2 | 25 | 22.9 | 8.5 |
| 3 | 25 | 21.8 | 12.7 |
| 4 | 25 | 28.4 | 13.5 |
| 5 | 25 | 16.2 | 35.3 |
| 6 | 25 | 15.8 | 37.0 |
| 7 | 25 | 35.5 | 41.8 |
| 8 | 25 | 46.5 | 85.8 |
| 9 | 25 | 27.7 | 10.8 |
| 10 | 25 | 32.3 | 29.1 |
| 11 | 25 | 26.1 | 4.3 |
| 12 | 25 | 25.3 | 1.0 |

TABLE XVI

Stool samples of male adult subjects spiked to a final concentration of 25 ng/mL

| Patient ID # | Actual Lactoferrin (ng/ML) | Estimated Lactoferrin (ng/mL) | Variation (%) |
|---|---|---|---|
| 1 | 25 | 21.9 | 12.4 |
| 2 | 25 | 21.2 | 15.0 |
| 3 | 25 | 20.9 | 16.3 |
| 4 | 25 | 21.4 | 14.4 |
| 5 | 25 | 20.8 | 16.8 |
| 6 | 25 | 22.8 | 8.8 |
| 7 | 25 | 28.9 | 15.5 |
| 8 | 25 | 29.4 | 17.4 |
| 9 | 25 | 36.7 | 47.0 |
| 10 | 25 | 19.5 | 21.9 |

A second method for spiking was using the same two stool specimens collected six weeks apart from six female and five male adults were diluted and spiked with lactoferrin to a concentration of 4 µg/mL. The "Estimated Lactoferrin" represents the level of lactoferrin determined from a standard curve generated by the quantitative ELISA. The % Variation represents the difference between the "Actual" amount used to spike the sample and the "Estimated" value. Under these conditions, the variation ranged from 11.3% to 84.9% for females and from 5.0% to 39.2% for males. Results were similar to those obtained with specimens spiked with 25 ng/mL lactoferrin as described above, showing a higher percent variation in female adults compared to male adults. The results are illustrated in Tables XVII and XVIII below.

TABLE XVII

Stool samples of female adult subjects spiked to a final concentration of 4 µg/mL

| Patient ID # | Actual Lactoferrin (µg/mL) | Estimated Lactoferrin (µg/mL) | Variation (%) |
|---|---|---|---|
| 1 | 4 | 4.5 | 11.3 |
| 2 | 4 | 4.6 | 15.3 |
| 3 | 4 | 5.3 | 33.4 |
| 4 | 4 | 4.9 | 21.4 |
| 5 | 4 | 3.5 | 11.5 |
| 6 | 4 | 3.4 | 14.7 |
| 7 | 4 | 5.3 | 32.7 |
| 8 | 4 | 6.7 | 67.6 |
| 9 | 4 | 5.5 | 38.6 |
| 10 | 4 | 5.8 | 44.9 |
| 11 | 4 | 5.8 | 43.9 |
| 12 | 4 | 7.4 | 84.9 |

TABLE XVIII

Stool samples of male adult subjects spiked to a final concentration of 4 µg/mL

| Patient ID # | Actual Lactoferrin (µg/mL) | Estimated Lactoferrin (µg/mL) | Variation (%) |
|---|---|---|---|
| 1 | 4 | 4.7 | 17.5 |
| 2 | 4 | 4.6 | 14.4 |
| 3 | 4 | 4.2 | 5.0 |
| 4 | 4 | 5.6 | 39.2 |
| 5 | 4 | 4.2 | 5.9 |
| 6 | 4 | 4.7 | 18.5 |
| 7 | 4 | 4.7 | 16.5 |
| 8 | 4 | 5.5 | 37.9 |
| 9 | 4 | 5.3 | 33.6 |
| 10 | 4 | 4.3 | 6.6 |

3. Monitoring Using the Quantitative ELISA

The quantitative ELISA of the present invention was used to follow the lactoferrin levels of single patient suffering from ulcerative colitis during a "flare" of active disease through remission. The patient showed extremely high levels of lactoferrin (e.g., 9749.37 µg/mL feces) during the peak of the active disease, the levels dropping rapidly (e.g., to 7.42 µg/mL feces) following anti-inflammatory drug therapy. Levels elevated dramatically again during a relapse and leveled at slightly above those of healthy control persons (e.g., 11.06 µg/mL feces) during periods of remission. Thus, lactoferrin levels determined according to the quantitative ELISA of the present invention accurately depicted disease activity in response to medical treatment.

In summary, the present invention is directed to non-invasive methods for differentiating between irritable bowel syndrome and inflammatory bowel disease using the presence of fecal lactoferrin as a detection marker for fecal leukocytes, and a kit used for such method. The present invention is further directed to immunoassays that utilize antibodies specific to human lactoferrin for the measurement of total endogenous lactoferrin in human feces. Still further, the present invention is directed to a quantitative immunoassay for monitoring the levels of fecal lactoferrin in a patient having IBD.

The immunoassays of the present invention are sensitive, specific and easy to perform. The assays detect lactoferrin, a stable protein that serves as a detection marker for fecal leukocytes and an indicator of intestinal inflammation, and quantitate fecal lactoferrin levels for monitoring patients having IBD. The tests are rapid and can be completed within about seventy-five minutes. Research results support the use of the qualitative ELISA as an in vitro diagnostic aid to help distinguish active IBD patients from those with active IBS. Research results further support the use of the quantitative ELISA for monitoring levels of fecal lactoferrin in patients having inflammatory diseases. The present invention has been described in relation to particular embodiments which are intended in all respects to be illustrative rather than restrictive. Alternative embodiments will become apparent to those skilled in the art to which the present invention pertains without departing from its scope.

From the foregoing, it will be seen that this invention is one well adapted to attain all the ends and objects herein above set forth together with other advantages which are obvious and which are inherent to the method. It will be understood that certain features and subcombinations are of utility and may be employed without reference to other features and subcombinations. This is contemplated by and is within the scope of the claims.

Having thus described the invention, what is claimed is:

1. A method for diagnosing irritable bowel syndrome, the method comprising:
   obtaining a fecal sample from a person presenting with symptoms common to inflammatory bowel disease and irritable bowel syndrome;
   diluting the sample;
   measuring the sample to determine the sample does not contain an elevated level of endogenous lactoferrin; and
   upon determining the sample does not contain an elevated level of endogenous lactoferrin, diagnosing the person with irritable bowel syndrome.

2. The method of claim 1, wherein the step of diluting said sample comprises diluting said sample to a 1:400 dilution factor.

3. The method of claim 1, wherein the step of measuring the sample to determine the sample does not contain an elevated level of endogenous lactoferrin comprises contacting the sample with immobilized polyclonal antibodies to human lactoferrin to create an antibody bound sample.

4. The method of claim 3, wherein the step of measuring the sample to determine the sample does not contain an elevated level of endogenous lactoferrin comprises contacting the antibody bound sample with enzyme-linked polyclonal antibodies such that the enzyme-linked polyclonal antibodies are allowed to bind to capture lactoferrin and create an enzyme-linked antibody bound sample.

5. The method of claim 4, wherein the step of measuring the sample to determine the sample does not contain an elevated level of endogenous lactoferrin comprises adding a substrate to the enzyme-linked antibody bound sample for color development to create a readable enzyme-linked antibody bound sample.

6. The method of claim 5, wherein the step of measuring the sample to determine the sample does not contain an elevated level of endogenous lactoferrin comprises determining an optical density of said readable enzyme-linked antibody bound sample at 450 nm, wherein the optical destiny corresponds to a level of endogenous lactoferrin in the readable enzyme-linked antibody bound sample.

7. The method of claim 6, wherein if said optical density of said readable enzyme-linked antibody bound sample is greater than 0.200, said sample contains an elevated level of endogenous lactoferrin.

8. A method for monitoring a human having inflammatory bowel disease for gastrointestinal inflammation, the method comprising:
   obtaining a first fecal sample from a human having inflammatory bowel disease at a first time;
   determining the concentration of endogenous lactoferrin in said first fecal sample to obtain a first lactoferrin concentration;
   obtaining a second fecal sample from the human having inflammatory bowel disease at a time later than the first time;
   determining the concentration of endogenous lactoferrin in said second fecal sample to obtain a second lactoferrin concentration; and
   comparing said first lactoferrin concentration to said second lactoferrin concentration to determine whether the human has had an increase or decrease in gastrointestinal inflammation.

9. The method of claim 8, further comprising:
   diluting said first and second samples.

10. The method of claim 9, further comprising:
    contacting said first sample with immobilized polyclonal antibodies to endogenous lactoferrin to create a first treated sample;
    contacting said first treated sample with enzyme-linked polyclonal antibodies to create a first enzyme-linked antibody bound sample;
    adding a substrate to the first enzyme-linked antibody bound sample to create a first readable sample; and
    determining the optical density of said first readable sample.

11. The method of claim 10, further comprising:
    contacting said second sample with immobilized polyclonal antibodies to endogenous lactoferrin to create a second treated sample;
    contacting said second treated sample with enzyme-linked polyclonal antibodies to create a second enzyme-linked antibody bound sample;
    adding a substrate to the second enzyme-linked antibody bound sample to create a second readable sample; and
    determining the optical density of said second readable sample.

12. The method of claim 10, further comprising:
    generating a purified lactoferrin standard curve and determining a linear portion of the standard curve.

13. The method of claim 12, wherein the step of diluting said fecal sample comprises diluting said first and second samples by serial tenfold dilutions until a measured result indicates a concentration of fecal lactoferrin that provides an optical density reading at 450 nm that is within the linear portion of the standard curve.

14. The method of claim 8, further comprising:
    monitoring the human for changing levels of fecal lactoferrin as an indicator of effectiveness of medical therapy.

* * * * *